United States Patent [19]

Anthony et al.

[11] Patent Number: 4,999,042
[45] Date of Patent: Mar. 12, 1991

[54] PHENYL OXIMINO-ACETATE FUNGICIDES

[75] Inventors: Vivienne M. Anthony, Maidenhead; John M. Clough, Marlow; Christopher R. A. Godfrey; Thomas E. Wiggins, both of Bracknell, all of England

[73] Assignee: Imperial Chemical Industries PLC, London, England

[21] Appl. No.: 452,333

[22] Filed: Dec. 19, 1989

Related U.S. Application Data

[63] Continuation of Ser. No. 382,058, Jul. 14, 1989, which is a continuation of Ser. No. 69,702, Jun. 30, 1987, abandoned.

[30] Foreign Application Priority Data

Jul. 18, 1986 [GB] United Kingdom ............... 8617648

[51] Int. Cl.$^5$ .................... A01N 37/10; A61K 31/24; C07C 251/48
[52] U.S. Cl. ......................................... 71/88; 71/90; 71/92; 71/94; 71/95; 71/98; 71/103; 71/105; 71/111; 514/114; 514/247; 514/255; 514/256; 514/274; 514/351; 514/352; 514/365; 514/367; 514/375; 514/427; 514/438; 514/448; 514/471; 514/538; 544/224; 544/318; 544/335; 544/336; 544/384; 546/300; 546/335; 548/178; 548/204; 548/217; 548/560; 549/72; 549/77; 549/487; 549/496; 558/172; 558/414; 560/9; 560/12; 560/22; 560/35
[58] Field of Search ............... 544/224, 316, 335, 336, 544/384; 546/300, 335; 548/178, 204, 217, 560; 549/72, 77, 487, 496; 558/172, 414; 560/9, 12, 22, 35; 71/88, 90, 92, 94, 95, 98, 103, 105, 111; 514/114, 247, 255, 256, 274, 351, 357, 365, 367, 375, 427, 438, 448, 471, 538

[56] References Cited

U.S. PATENT DOCUMENTS 4,581,060  4/1986  Martin ........................... 71/94
4,829,085  5/1989  Wenderoth et al. ............ 514/522

Primary Examiner—Richard L. Raymond
Attorney, Agent, or Firm—Cushman, Darby & Cushman

[57] ABSTRACT

Compounds of the fomrula (I):

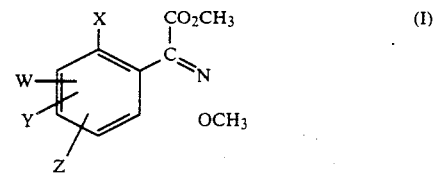

and sterioisomers thereof, wherein X is halogen, alkyl, cycloalkyl, aralkyl, aryloxyalkyl, alkenyl, alkynyl, aryl, amino, arylazo, heteroarylalkyl, heteroaryloxyalkyl, acylamino nitro, nitride, trifluoromethyl, $-OR^1$, $-SR^1$, $-CO_2R^2$, $-CONR^3R^4$, $-COR^5$, $-CR^6=NR^7$, $-N=CR^8R^9$, $-SOR^{10}$ or $-SO_2R^{11}$; W, Y and Z, which may be the same or different, are any of the atoms or groups listed for X above and, in addition, may be hydrogen atoms; or any two of the groups W, X, Y and Z, in adjacent positions on the phenyl ring, optionally join to form a fused ring, either aromatic or aliphatic, optionally containing one or more heteroatoms; $R^1$ is alkyl, or cycloalkyl optionally containing a heteroatom in the cycloalkyl ring, alkenyl, acyl, aryl, heteroaryl, aralkyl or heteroarylalkyl; $R^2$, $R^3$, $R^4$, $R^5$, $R^6$, $R^8$, $R^9$, $R^{10}$ and $R^{11}$, which may be the same or different, are hydrogen or alkyl, cycloalkyl, cycloalkylalkyl, alkenyl, aralkyl, aryl or heteroaryl; and $R^7$ is aryl, the alkyl, cycloalkyl, aralkyl, aryloxyalkyl, alkeny, alkynyl, aryl, amino, arylazo, heteroarylalkyl, heteroaryloxyalkyl, acylamino, acyl, and heteroaryl being optionally substituted. The compounds are useful as fungicides and as plant growth regulators.

8 Claims, No Drawings

PHENYL OXIMINO-ACETATE FUNGICIDES

This is a continuation of Application No. 07/382,058, filed Jul. 14, 1989 which is a continuation of Ser. No. 07/069,702, filed Jun. 30, 1987, now abandoned, pending.

This invention relates to derivatives of acrylic acid useful in agriculture (especially as fungicides but also as plant growth regulators) to processes for preparing them, to agricultural (especially fungicidal) compositions containing them, and to methods of using them to combat fungi, especially fungal infections in plants, and to regulate plant growth.

The invention provides a compound having the general formula (I):

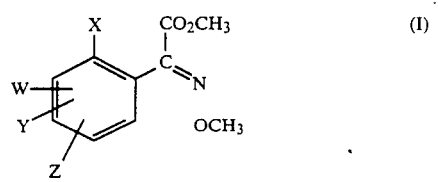

and stereoisomers thereof, wherein X is halogen (fluorine, chlorine, bromine or iodine), optionally substituted alkyl, optionally substituted cycloalkyl, optionally substituted aralkyl, optionally substituted aryloxyalkyl, optionally substituted alkenyl, optionally substituted alkynyl, optionally substituted aryl, optionally substituted amino, optionally substituted arylazo, optionally substituted heteroarylalkyl, optionally substituted heteroaryloxyalkyl, optionally substituted acylamino, nitro, nitrile, $-OR^1$, $-SR^1$, $-CO_2R^2$, $-CONR^3R^4$, $-COR^5$, $-CR^6=NR^7$, $-N=CR^8R^9$, $-SOR^{10}$ or $-SO_2R^{11}$; W, Y and Z, which may be the same or different, are any of the atoms or groups listed for X above and, in addition, may be hydrogen atoms; or any two of the groups W, X, Y and Z, in adjacent positions on the phenyl ring, optionally join to form a fused ring, either aromatic or aliphatic, optionally containing one or more heteroatoms; $R^1$ is optionally substituted alkyl, or cycloalkyl optionally containing a hetero atom in the cycloalkyl ring, optionally substituted alkenyl, optionally substituted acyl, optionally substituted aryl, optionally substituted heteroaryl, optionally substituted aralkyl, or optionally substituted heteroarylalkyl; $R^2$, $R^3$, $R^4$, $R^5$, $R^6$, $R^8$, $R^9$, $R^{10}$ and $R^{11}$, which may be the same or different, are hydrogen or optionally substituted alkyl, cycloalkyl, cycloalkylalkyl, optionally substituted alkenyl, optionally substituted aralkyl, optionally substituted aryl or optionally substituted heteroaryl; and $R^7$ is optionally substituted aryl.

Of particular interest are those compounds of formula (I) in which X is optionally substituted aralkyl, optionally substituted heteroarylalkyl, optionally substituted aryloxyalkyl, optionally substituted heteroaryloxyalkyl, optionally substituted alkenyl (especially optionally substituted aryl- or optionally substituted heteroaryl-ethenyl), optionally substituted alkynyl (especially optionally substituted aryl- or optionally substituted heteroaryl-ethynyl), optionally substituted acylamino (especially optionally substituted aryl- or optionally substituted heteroaryl-carbonylamino), $-OR^1$, $-SR^1$ or $-CO_2R^2$; W, Y and Z, which are the same or different, are single atoms or sterically small groups such as fluoro, chloro, bromo, hydroxy, methyl, methoxy, trifluoromethyl, methylamino or dimethylamino but are preferably hydrogen; or W and X, when in adjacent positions on the phenyl ring, join to form a fused ring, either aromatic or aliphatic, optionally containing one or more heteroatoms; $R^1$ is optionally substituted aryl, optionally substituted heteroaryl, optionally substituted aralkyl or optionally substituted heteroarylalkyl and $R^2$ is optionally substituted alkyl (especially $C_{1-4}$ alkyl) or optionally substituted aryl.

The compounds of the invention contain at least one carbon-nitrogen double bond, and are sometimes obtained in the form of mixtures of geometric isomers. However, these mixtures can be separated into individual isomers, and this invention embraces such isomers, and mixtures thereof in all proportions including those which consist substantially of the (E)-isomer and those which consist substantially of the (Z)-isomer.

The individual stereoisomers which result from the unsymmetrically substituted double bond of the oxime ether group are identified by the commonly used terms "(E)" and "(Z)". These terms are defined according to the Cahn-Ingold-Prelog system which is fully described in the literature (see, for example, J March, "Advanced Organic Chemistry" 3rd edition, Wiley-Interscience, Page 109 et seq).

The use hereinafter of the formula:

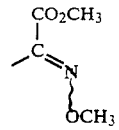

signifies a separable mixture of both geometric isomers about the carbon-nitrogen double bond of the oxime ether, i.e.

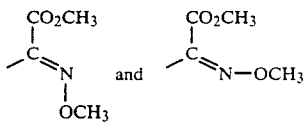

Geometric pairs of isomers of the compounds listed later in Table I are identified by the letters A and B. In many instances, using solvent systems such as ether or ethyl acetate, or mixtures of one of these with petrol, the isomers A and B of a compound have significantly different $R_f$ values when analysed by thin-layer chromatography on silica gel. Of each pair of isomers the isomer which is the less polar on silica gel is termed Isomer A and the more polar one, Isomer B. In the case of the two geometric isomers of methyl 0-methyl(2-phenoxyphenyl)oximino-acetate (compounds numbers 5 and 6 of Table I), Isomer B has been shown unambiguously by X-ray analysis to be the (E)-isomer. It is believed that for every isomer pair, Isomer B corresponds to the (E)-isomer and Isomer A corresponds to the (Z)-isomer but this has not been proven. Generally the B isomers are the more active ones fungicidally and form a preferred embodiment of the invention.

In the compounds of formula (I), alkyl groups and alkyl moieties in, for example, "alkoxy", "alkylthio", "aralkyl" and "heteroaryloxyalkyl" groups can be in the form of straight or branched chains and preferably contain 1 to 6 carbon atoms, more preferably 1 to 4 carbon atoms. Examples are methyl, ethyl, propyl (n-and iso-propyl) and butyl (n-, sec-, iso- and tertbutyl). Optional substituents of alkyl include hydroxy, halogen (especially chlorine or fluorine), and alkoxycarbonyl. Trifluoromethyl is a particular example of optionally substituted alkyl. Cycloalkyl is preferably $C_{3-6}$ cycloalkyl and includes cyclohexyl. An example of a cycloalkyl group containing a hetero-atom is tetrahydropyranyl. Cycloalkylalkyl is preferably $C_{3-6}$ cycloalkyl($C_{1-4}$)alkyl, for example, cyclopropylethyl.

Aralkyl includes, particularly, phenylalkyl (especially benzyl, phenylethyl, phenylpropyl, phenylbutyl or phenylhexyl) in which the alkyl moiety may carry other substituents such as hydroxy or $C_{1-4}$ alkoxy and the aryl moiety may be substituted with, for example, one or more of halogen (especially chlorine or fluorine), hydroxy, $C_{1-4}$ alkyl (especially methyl), $C_{1-4}$ alkoxy (especially methoxy), trifluoromethyl, trifluoromethoxy, optionally substituted phenoxy, optionally substituted benzyloxy, nitro, amino, phenyl, carboxy or a carboxylic acid ester, cyano, alkylcarbonylamino and methylenedioxy. Substituents which may be present on the phenoxy and benzyloxy groups include any of those other substituents which may be present on the aryl moiety of aralkyl.

Aryloxyalkyl includes, in particular, phenoxyalkyl (especially phenoxymethyl and phenoxyethyl) in which the alkyl moiety may carry other substituents such as methoxy and the aryl moiety may be substituted in the same way as the aryl moiety in aralkyl above.

Alkenyl and alkynyl groups preferably contain 2 to 6 carbon atoms and, more preferably, 2 to 4 carbon atoms in the form of straight or branched chains. Ethenyl, propenyl and butenyl are examples of alkenyl groups. Optional substituents of alkenyl include aromatic and heteroaromatic groups (such as phenyl, furyl, thienyl and pyridyl) which may themselves carry substituents such as those described for the aryl moiety of aralkyl above. These include halogen (especially chlorine or fluorine). Further, the terminal carbon atom of the alkenyl groups may form part of a 5- or 6-membered cycloalkyl group. Alkynyl includes ethynyl and is optionally substituted by, for example, phenyl which may itself be substituted as for the aryl moiety of aralkyl above.

Aryl is preferably phenyl. It may be substituted in the same way as the aryl moiety of aralkyl above.

Optional substituents which may be carried by an amino group include one or two of N-aryl and N-alkyl groups (such as N-phenyl or N-methyl).

Arylazo is, for example, phenylazo in which the aryl moiety is optionally substituted by, for example, alkynyl, alkoxy (especially methoxy) or dialkylamino (especially dimethylamino).

Heteroaryl wherever it appears (as a substituent on its own or as part of another substituent such as "heteroaryloxy-alkyl") includes 5- and 6-membered heteroaromatic ring systems which may be fused with one or more other aromatic or heteroaromatic rings. Examples are pyridyl, pyrimidinyl, pyrazinyl, pyridazinyl, furyl, thienyl, pyrrolyl, thiazolyl, benzoxazolyl and benzthiazolyl. Optional substituents include those described for the aryl moiety of aralkyl above.

Acyl includes, in particular, acetyl and benzoyl, and acylamino includes benzoylamino, furoylamino and thienylcarbonylamino optionally substituted by, for example, N-alkyl (especially N-methyl).

In one particular aspect, the invention includes compounds of formula (I) in which X is a group Ar-A- wherein A is a linking group such as O, S, CHR'-CHR", CH=CH, C≡C, OCHR', CHR'O, $O_2^C$ or CONR', R' and R" are independently methyl or, preferably, hydrogen and Ar is aryl (for example phenyl or naphthyl), heteroaryl (for example furyl, thienyl, pyridyl, pyrimidinyl or pyrazinyl) or cyclohexyl, the aryl and heteroaryl moieties being optionally substituted with, for example, one or more of halo (especially fluoro or chloro), methyl, methoxy or nitro; and W, Y and Z are preferably hydrogen or one or more are single atoms such as fluorine or chlorine or sterically small groups such as methyl or methoxy, or when W is in an adjacent position to X on the phenyl ring, Ar is phenyl and A is O or S, W joins Ar at the carbon atom adjacent to that attached to A, optionally via a linking oxygen or sulphur atom, to form a fused ring.

Preferably A is O or CH=CH and Ar is furyl or phenyl optionally substituted with fluoro, chloro, methoxy or nitro and W, Y and Z are hydrogen.

The invention is illustrated by the compounds listed in Table I which follows.

TABLE I

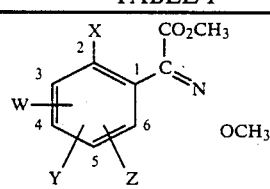

| COMPOUND NO | X | W | Y | Z | MELTING POINT (°C.) | ISOMER* |
|---|---|---|---|---|---|---|
| 1 | (E)-C6H5CH:CH | H | H | H | Oil | A |
| 2 | (E)-C6H5CH:CH | H | H | H | 77-78 | B |
| 3 | (E)-2-C4H3O.CH:CH | H | H | H | Oil | A |
| 4 | (E)-2-C4H3O.CH:CH | H | H | H | 87-88 | B |
| 5 | C6H5O | H | H | H | Oil | A |
| 6 | C6H5O | H | H | H | 108-111 | B |
| 7 | 4-NO2—C6H4O | H | H | H | 99-99.5 | B+ |
| 8 | 2,4-di-NO2—C6H3O | H | H | H | Oil | A |
| 9 | 2,4-di-NO2—C6H3O | H | H | H | 131-133 | B |
| 10 | C6H11O | H | H | H | Oil | A |
| 11 | C6H11O | H | H | H | Oil | B |
| 12 | C6H5CONH | H | H | H | 153 | B+ |
| 13 | 2-C4H3O.CONH | H | H | H | 98 | A |
| 14 | 2-C4H3O.CONH | H | H | H | 138-139 | B |
| 15 | 2-C4H3S.CONH | H | H | H | 103 | A |

TABLE I-continued

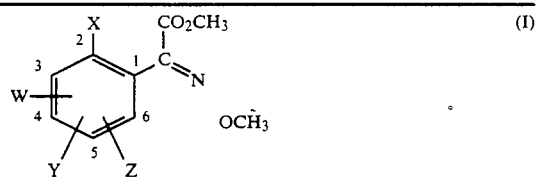

| COMPOUND NO | X | W | Y | Z | MELTING POINT (°C.) | ISOMER* |
|---|---|---|---|---|---|---|
| 16 | 2-$C_4H_3$S.CONH | H | H | H | 139–140 | B |
| 17 | φ | φ | H | H | Oil | A |
| 18 | φ | φ | H | H | 119–120 | B |
| 19 | $C_6H_5$O | 5-F | H | H | | A |
| 20 | $C_6H_5$O | 5-F | H | H | | B |
| 21 | 3-F—$C_6H_4$O | H | H | H | | A |
| 22 | 3-F—$C_6H_4$O | H | H | H | | B |
| 23 | 4-F—$C_6H_4$O | H | H | H | | A |
| 24 | 4-F—$C_6H_4$O | H | H | H | | B |
| 25 | 3-Cl—$C_6H_4$O | H | H | H | | A |
| 26 | 3-Cl—$C_6H_4$O | H | H | H | | B |
| 27 | 4-MeO—$C_6H_4$O | H | H | H | | A |
| 28 | 4-MeO—$C_6H_4$O | H | H | H | | B |
| 29 | $C_6H_5CH_2CH_2$ | H | H | H | | A |
| 30 | $C_6H_5CH_2CH_2$ | H | H | H | | B |
| 31 | φ | φ | H | H | Oil | A |
| 32 | φ | φ | H | H | Oil | B |
| 33 | 2-$C_4H_3$S.CON($CH_3$) | H | H | H | 166 | B+ |
| 34 | $C_6H_5$.O$CH_2$ | H | H | H | | A |
| 35 | $C_6H_5$.O$CH_2$ | H | H | H | | B |
| 36 | 2-$CH_3$—$C_6H_4$.O$CH_2$ | H | H | H | | A |
| 37 | 2-$CH_3$—$C_6H_4$.O$CH_2$ | H | H | H | | B |
| 38 | 3-Cl—$C_6H_4$.O$CH_2$ | H | H | H | | A |
| 39 | 3-Cl—$C_6H_4$.O$CH_2$ | H | H | H | 53–54 | B+ |
| 40 | 4-$CH_3$O—$C_6H_4$.O$CH_2$ | H | H | H | | A |
| 41 | 4-$CH_3$O—$C_6H_4$.O$CH_2$ | H | H | H | | B |
| 42 | 3-Cl—$C_6H_4$.OCH($CH_3$) | H | H | H | | A |
| 43 | 3-Cl—$C_6H_4$.OCH($CH_3$) | H | H | H | | B |
| 44 | $CH_3$ | H | H | H | | A |
| 45 | $CH_3$ | H | H | H | 64–65 | B+ |
| 46 | Br$CH_2$ | H | H | H | | A |
| 47 | Br$CH_2$ | H | H | H | | B |
| 48 | ($CH_3CH_2$O)$_2$P(O)$CH_2$ | H | H | H | | A |
| 49 | ($CH_3CH_2$O)$_2$P(O)$CH_2$ | H | H | H | | B |
| 50 | (E)-4-F—$C_6H_4$.CH:CH | H | H | H | | A |
| 51 | (E)-4-F—$C_6H_4$.CH:CH | H | H | H | | B |
| 52 | $C_6H_5CH_2$O | H | H | H | | A |
| 53 | $C_6H_5CH_2$O | H | H | H | | B |
| 54 | 3,5-di-Cl—$C_6H_3CH_2$O | H | H | H | | A |
| 55 | 3,5-di-Cl—$C_6H_3CH_2$O | H | H | H | | B |
| 56 | $C_6H_5$.O$CH_2$ | 3-F | 5-F | 6-F | | A |
| 57 | $C_6H_5$.O$CH_2$ | 3-F | 5-F | 6-F | | B |
| 58 | 2-pyridyl-O— | H | H | H | | A |
| 59 | 2-pyridyl-O— | H | H | H | | B |
| 60 | 5-Cl-2-pyridyl-O— | H | H | H | | A |
| 61 | 5-Cl-2-pyridyl-O— | H | H | H | | B |

TABLE I-continued (I) Structure: phenyl ring with positions 2(X), 3, 4(W), 5(Y), 6(Z), and at position 1 a C(CO₂CH₃)=N−OCH₃ group.

| COMPOUND NO | X | W | Y | Z | MELTING POINT (°C.) | ISOMER* |
|---|---|---|---|---|---|---|
| 62 | 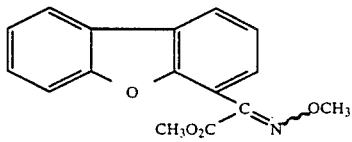 (6-chloropyrazinyl-methoxy) | H | H | H | | A |
| 63 | (same as 62) | H | H | H | | B |
| 64 | 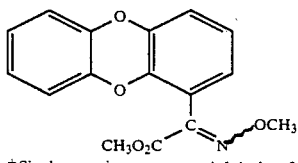 (6-chloropyrimidinyl-methoxy) | H | H | H | | A |
| 65 | (same as 64) | H | H | H | | B |
| 66 | $C_6H_5.S$ | H | H | H | | A |
| 67 | $C_6H_5.S$ | H | H | H | | B |
| 68 | $C_6H_5.C{:}C$ | H | H | H | | A |
| 69 | $C_6H_5.C{:}C$ | H | H | H | | B |
| 70 | $C_6H_5.O_2C$ | H | H | H | | A |
| 71 | $C_6H_5.O_2C$ | H | H | H | | B |
| 72 | $CH_3O_2C$ | H | H | H | | A |
| 73 | $CH_3O_2C$ | H | H | H | 138 | B+ |

*The refers to the geometry about the carbon-nitrogen double bond. Isomer A is the less polar of the 2 isomers on silica gel.
$C_6H_5$ is a phenyl group.
$C_6H_{11}O$ is a cyclohexyloxy group.
$C_4H_3O$ is a furyl group.
$C_4H_3S$ is a thienyl group.
φ Substituents join to form a fused ring. Thus compounds 17 and 18 are isomers of

[dibenzofuran substituted with $CH_3O_2C-C(=N-OCH_3)$ group]

and compounds 31 and 32 are isomers of

[dibenzodioxin substituted with $CH_3O_2C-C(=N-OCH_3)$ group]

+Single stereoisomer prepared. It is therefore uncertain whether this is isomer A or B. For compound number 45, see comments in Example 3.

TABLE II

SELECTED PROTON NMR DATA

TABLE II shows selected proton NMR data for certain compounds described in TABLE I. Chemical shifts are measured in ppm from tetramethylsilane, and deuterochloroform was used as solvent throughout. The following abbreviations are used:

| br | = | broad | t | = | triplet |
|---|---|---|---|---|---|
| s | = | singlet | q | = | quartet |
| d | = | doublet | m | = | multiplet |
| J | = | coupling constant | Hz | = | Hertz |

| COMPOUND NO | DATA |
|---|---|
| 1 | 3.78 (3H,s); 4.03 (3H,s); 7.01 (1H,d J 16Hz); 7.24–7.56 (9H,m); 7.68 (1H,d J 8Hz) ppm |

TABLE II-continued
SELECTED PROTON NMR DATA

| | |
|---|---|
| 2 | 3.82 (3H,s); 4.03 (3H,s); 6.87 (1H,d J 16Hz); 7.06 (1H,d J 16Hz); 7.14–7.48 (8H,m); 7.74 (1H,d J 8Hz) ppm. |
| 3 | 3.83 (3H,s); 4.07 (3H,s) ppm. |
| 4 | 3.86 (3H,s); 4.06 (3H,s); 6.35 and 6.42 (each 1H, apparently d J 5Hz); 6.79 and 6.86 (each 1H, d J 16 Hz); 7.66 (1H, d J 8Hz) ppm. |
| 5 | 3.63 (3H,s); 4.01 (3H,s) ppm. |
| 6 | 3.76 (3H,s); 4.00 (3H,s) ppm. |
| 7 | 3.78 (3H,s); 3.96 (3H,s); 7.0–7.1 (3H,m); 7.3–7.5 (3H,m); 8.21 (2H, d J 8Hz) ppm. |
| 8 | 3.77 (3H,s); 3.94 (3H,s); 6.86 (1H, d J 10Hz); 7.13 (1H, d J 8Hz); 7.42 (1H,m); 7.56 (1H,m); 7.83 (1H, dd J 8 and 1Hz), 8.30 (1H, dd J 8 and 2Hz); 8.89 (1H, d J 2Hz) ppm. |
| 9 | 3.84 (3H,s); 3.99 (3H,s), 7.06 (1H, d J 10Hz); 7.16 (1H, d J 8Hz); 7.42 (2H,m), 7.55 (1H,m); 8.29 (1H, dd J 10 and 2Hz); 8.82 (1H, d J 2Hz) ppm. |
| 10 | 3.80 (3H,s); 3.96 (3H,s); 4.2 (1H,brs); 6.60–7.60 (4H,m) ppm. |
| 11 | 3.80 (3H,s); 3.96 (3H,s); 4.2 (1H,brs); 6.75–7.20 (4H,m) ppm. |
| 12 | 3.78 (3H,s); 4.03 (3H,s); 7.1–8.3 (10H,m) ppm. |
| 13 | 3.90 (3H,s); 4.11 (3H,s); 6.48 (1H, dd J 4 and 2Hz); 7.0–7.5 (5H,m); 8.81 (1H,d J 8Hz); 9.8 (1H,brs) ppm. |
| 14 | 3.81 (3H,s); 4.11 (3H,s); 6.48 (1H,dd J 4 and 2Hz); 7.1–7.5 (5H,m); 8.10 (1H,d J 9Hz); 8.3 (1H,brs) ppm. |
| 15 | 4.00 (3H,s); 4.12 (3H,s), 7.0–7.8 (6H,m); 8.80 (1H,d J 8Hz), 11.1 (1H,s) ppm. |
| 16 | 3.88 (3H,s); 4.18 (3H,s), 7.0–7.3 (6H,m); 8.05 (1H,d J 8Hz); 8.1 (1H,s) ppm. |
| 17 | 4.02 (3H,s); 4.11 (3H,s); 7.3–7.4 (2H,m); 7.42–7.56 (2H,m); 7.81 (1H, d J 8Hz); 7.9–8.02 (2H,m) ppm. |
| 18 | 3.91 (3H,s); 4.10 (3H,s); 7.32–7.52 (4H,m); 7.54 (1H, d J 8Hz); 7.92–8.06 (2H,m) ppm. |
| 31 | 3.92 (3H,s); 4.04 (3H,s); 6.72–6.96 (6H,m); 7.25–7.35 (1H,m) ppm. |
| 32 | 3.87 (3H,s); 4.08 (3H,s); 6.74–6.98 (7H,m) ppm. |
| 33 | 3.3 (3H,s); 3.7 (3H,s); 3.82 (3H,s); 6.56–7.62 (7H,m) ppm. |

The compounds of the invention having the general formula (I) can be prepared by the routes shown in Scheme I. Throughout Scheme I the terms W, X, Y and Z are as defined above, L is a halogen atom (a bromine, iodine or chlorine atom), and M is a metal atom (such as a lithium atom) or a metal atom plus an associated halogen atom (such as MgI, MgBr or MgCl).

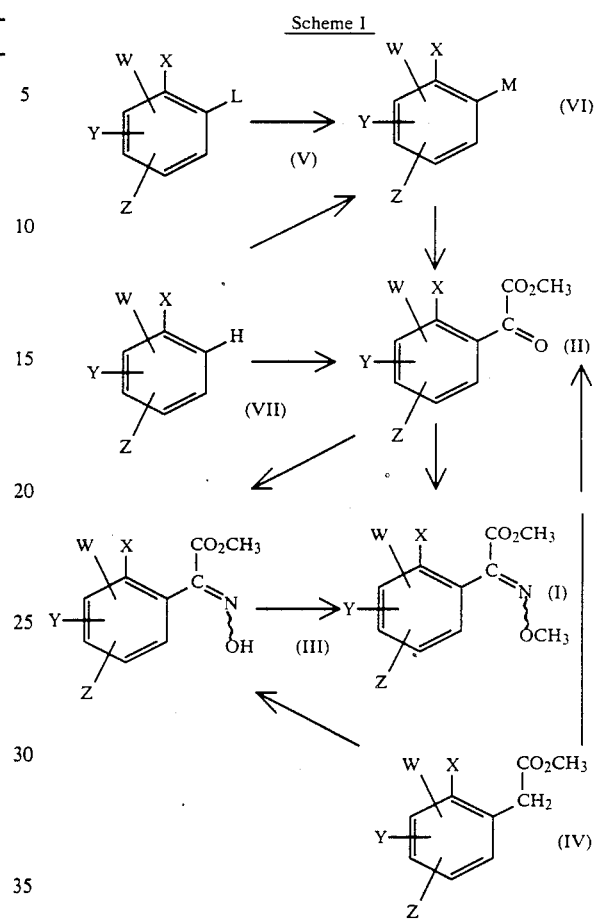

Scheme I

Thus compounds of the invention having the general formula (I) can be prepared by treating ketoesters of general formula (II) with methoxylamine (or a salt of methoxylamine) in a suitable solvent and at a suitable temperature.

Alternatively, compounds of the invention having the general formula (I) can be prepared by methylation of oximes of general formula (III) using a methylating agent such as a methyl halide (methyl iodide, methyl bromide or methyl chloride) or dimethyl sulphate, usually in the presence of a base such as sodium methoxide, in a suitable solvent and at a suitable temperature (see, for example, H. S. Anker and H. T. Clarke, *Organic Syntheses*, Collective Vol. 3, 172). Diazomethane may also be used for this O-methylation.

Oximes of general formula (III) can be prepared by treatment of ketoesters of general formula (II) with hydroxylamine (or a salt of hydroxylamine) in a suitable solvent and at a suitable temperature.

Alternatively, oximes of general formula (III) can be prepared by nitrosation of phenylacetates of general formula (IV) using nitrous acid or an ester of nitrous acid, usually in the presence of a base such as sodium methoxide, in a suitable solvent and at a suitable temperature (see, for example, O. Touster, *Organic Reactions*, 1953, 7, 327, particularly page 342 and S Kukolja, S E Draheim, B J Graves, D C Hunden, J L Pfeil, R D G Cooper, J L Ott, and F T Counter, *J. Med. Chem.*, 1985, 28, 1896).

Other methods for the preparation of oximes (III) have been reported in the chemical literature (see, for example, T Shimizu, Y Hayashi and K Teramura, *Bull. Chem. Soc. Jpn.*, 1985, 58, 2519; G W Shaffer, *Can. J. Chem.*, 1970, 48, 1948).

Ketoesters of general formula (II) can be prepared by the following methods. Each transformation is often performed in a convenient solvent.
(i) By treatment of metallated species of general formula (VI) with dimethyl oxalate (see for example, EP-A-0178826).
(ii) By Friedel-Crafts acylation of substituted benzenes (VII) using methyl oxalyl chloride in the presence of an acid, especially a Lewis acid, in catalytic or stoichiometric amounts.
(iii) By oxidation of phenylacetates of general formula (IV) using, for example, selenium dioxide.

Halobenzenes of general formula (V), benzenes of general formula (VII), and phenylacetates of general formula (IV) can be made by standard procedures described in the chemical literature.

In all of the methods described above, the function $CH_3O_2C.C:N.OCH_3$ is constructed from precursors in which the groups W, X, Y and Z are already intact. It is also possible to construct the function $CH_3O_2C.C:N.OCH_3$ and then to modify the groups W, X, Y and Z. For example, in a compound (I) wherein X is a methyl group, it is possible to convert this methyl group first into a bromomethyl group by treatment with N-bromosuccinimide, then into a phosphonomethyl group by treatment with a trialkyl phosphite, and then into a styryl group by treatment with a base and then benzaldehyde (cf. EP-A-0203606). When such a method is used to make compounds in which W, Y and Z are all hydrogen, Compounds 44 to 49 of Table I are key intermediates.

In further aspects the invention provides processes as herein described for preparing the compounds of formula (I). It also provides the intermediate chemical of formula (III) and, as intermediate chemicals, Compounds 44 to 49 of Table I.

The compounds of the invention are active fungicides, and may be used to control one or more of the following pathogens:

*Pyricularia oryzae* on rice.

*Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants.

*Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apples and *Uncinula necator* on vines.

*Helminthosporium* spp., *Rhynchosporium* spp., *Septoria* spp., and *Pseudocercosporella herpotrichoides* on cereals. *Cercospora arachidicola* and *Cercosporidium personata* on peanuts and other *Cercospora* species on other hosts for example sugar beet, bananas, soya beans and rice.

*Venturia inaequalis* (scab) on apples.

*Plasmopara viticola* on vines.

Other downy mildews such as *Bremia lactucae* on lettuce, *Peronospora* spp. on soybeans, tobacco, onions and other hosts and *Pseudoperonospora humuli* on hops and *Pseudoperonospora cubensis* on cucurbits.

*Phytophthora infestans* on potatoes and tomatoes and other *Phytophthora* spp. on vegetables, strawberries, avocado, pepper, ornamentals, tobacco, cocoa and other hosts.

Some of the compounds have also shown a broad range of activities against fungi in vitro.

Some of the compounds may also have activity against various post-harvest pathogens of fruit (e.g. *Penicillium digitatum* and *italicum* and *Trichoderma viride* on oranges, *Gloeosporium musarum* on bananas and *Botrytis cinerea* on grape).

The compounds may also be useful as industrial (as opposed to agricultural) fungicides, e.g. in the prevention of fungal attack on wood, hides, leather and especially paint films.

The compounds may move locally in plant tissue. Moreover, the compounds may be volatile enough to be active in the vapour-phase against fungi on the plant.

Therefore in another aspect the invention provides a method of combating fungi, which comprises applying to a plant, to a seed of a plant, or to the locus of the plant or seed, a fungicidally effective amount of a compound of formula (I) as hereinbefore defined, or a composition containing the same.

Some compounds exhibit plant growth regulating activity and may be deployed for this purpose, again at appropriate rates of application.

Therefore, in yet another aspect the invention provides a method of regulating plant growth which comprises applying to a plant an effective amount of a plant growth regulating compound of formula (I).

The compounds may be used directly for agricultural purposes but are more conveniently formulated into compositions using a carrier or diluent. The invention thus provides a fungicidal or plant growth regulator composition comprising an effective amount of a compound of formula (I) as hereinbefore defined, and an acceptable carrier or diluent therefor.

The compounds can be applied in a number of ways. For example they can be applied, formulated or unformulated, directly to the foliage of a plant, to seeds or to other medium in which plants are growing or are to be planted. They can be sprayed on, dusted on or applied as a cream or paste formulation; or they can be applied as a vapour or as slow release granules. Application can be to any part of the plant including the foliage, stems, branches or roots, or to soil surrounding the roots, or to the seed before it is planted; or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example fillers such as kaolin, bentonite, kieselguhr, dolomite, calcium carbonate, talc, powdered magnesia, Fuller's earth, gypsum, diatomaceous earth and China clay. Such granules can be preformed granules suitable for application to the soil without further treatment.

These granules can be made either by impregnating pellets of filler with the active ingredient or by pelleting a mixture of the active ingredient and powdered filler. Compositions for dressing seed may include an agent (for example a mineral oil) for assisting the adhesion of the composition to the seed; alternatively the active ingredient can be formulated for seed dressing purposes using an organic solvent (for example N-methylpyrrolidone, propylene glycol or dimethylformamide). The compositions may also be in the form of wettable powders or water dispersible granules comprising wetting or dispersing agents to facilitate their dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent and including a suspending agent to stop the solid settling.

Compositions to be used as sprays may be in the form of aerosols wherein the formulation is held in a container under pressure in the presence of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The inclusion of a photostabiliser may enhance the persistence of the compounds in their biological effect. Suitable stabilisers may include the commercially available benzotriazole stabilisers, such as 2-(2'-hydroxy-5'-methylphenyl)benzotriazole, and benzophenone stabilisers, such as 2-hydroxy-4-methoxybenzophenone.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants e.g. a wetting agent, dispersing agent, emulsifying agent or suspending agent. These agents can be cationic, anionic or non-ionic agents.

Suitable cationic agents are quaternary ammonium compounds, for example cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which possess plant growth regulating, herbicidal or insecticidal activity.

A fungicidal compound which may be present in the composition of the invention may be one which is capable of combating ear diseases of cereals (e.g. wheat) such as *Septoria, Gibberella* and *Helminthosporium* spp., seed and soil borne diseases and downy and powdery mildews on grapes and powdery mildew and scab on apple etc. By including another fungicide the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are carbendazim, benomyl, thiophanate-methyl, thiabendazole, fuberidazole, etridazole, dichlofluanid, cymoxanil, oxadixyl, ofurace, metalaxyl, furalaxyl, benalaxyl, fosetyl-aluminium, fenarimol, iprodione, prothiocarb, procymidone, vinclozolin, penconazole, myclobutanil, propamocarb, R0151297, diconazole, pyrazophos, ethirimol, ditalimfos, buthiobate, tridemorph, triforine, nuarimol, triazbutyl, guazatine, triacetate salt of 1,1'-iminodi-(octamethylene)diguanidine, propiconazole, prochloraz, 4-chloro-N-(1-cyano-1-ethoxymethyl)benzamide, flutriafol, hexaconazole, (2RS,3RS)-2-(4-chlorophenyl)-3-cyclopropyl-1-(1H-1,2,4-triazol-1H-1,2,4-triazol-1-yl)butan-2-ol, (RS)-1-(4-chlorophenyl)-

4,4-dimethyl-3-(1H-1,2,4-triazol-1-ylmethyl)pentan-3-ol, DPX H6573 (1-((bis-4-fluorophenyl)methylsilyl)methyl)-1H-1,2,4-triazole, triadimefon, triadimenol, diclobutrazol, fenpropimorph, pyrifenox, fenpropidin, chlorozolinate, imazalil, fenfuram, carboxin, oxycarboxin, methfuroxam, dodemorph, BAS 454, blasticidin S, kasugamycin, edifenphos, Kitazin P, cycloheximide, phthalide, probenazole, isoprothiolane, tricyclazole, pyroquilon, chlorbenzthiazone, neoasozin, polyoxin D, validamycin A, mepronil, flutolanil, pencycuron, diclomezine, phenazin oxide, nickel dimethyldithiocarbamate, techlofthalam, bitertanol, bupirimate, etaconazole, hydroxyisoxazole, streptomycin, cyprofuram, biloxazol, quinomethionate, dimethirimol, 1-(2-cyano-2-methoxyiminoacetyl)-3-ethyl urea, fenapanil, tolclofos-methyl, pyroxyfur, polyram, maneb, mancozeb, captafol, chlorothalonil, anilazine, thiram, captan, folpet, zineb, propineb, sulphur, dinocap, dichlone, chloroneb, binapacryl, nitrothal-isopropyl, dodine, dithianon, fentin hydroxide, fentin acetate, tecnazene, quintozene, dichloran, copper containing compounds such as copper oxychloride, copper sulphate and Bordeaux mixture, and organomercury compounds.

The compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophas, buprofezin, ethroproxyfen and cycloprothrin.

Plant growth regulating compounds are compounds which control weeds or seedhead formation, or selectively control the growth of less desirable plants (e.g. grasses).

Examples of suitable plant growth regulating compounds for use with the invention compounds are the gibberellins (eg. GA$_3$, GA$_4$ or GA$_7$), the auxins (eg. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acids (e.g. triiodobenzoic acid), morphactins (e.g. chlorfluoroecol), maleic hydrazide, glyphosate, glyphosine, long chain fatty alcohols and acids, dikegulac, paclobutrazol, flurprimidol, fluoridamid, mefluidide, substituted quaternary ammonium and phosphonium compounds (e.g. chloromequat chlorphonium or mepiquatchloride), ethephon, carbetamide, methyl-3,6-dichloroanisate, daminozide, asulam, abscisic acid, isopyrimol, 1-(4-chlorophenyl)-4,6-dimethyl-2-oxo-1,2-dihydropyridine-3-carboxylic acid, hydroxybenzonitriles (e.g. bromoxynil), difenzoquat, benzoylprop-ethyl 3,6-dichloropicolinic acid, fenpentezol, inabenfide, triapenthenol and tecnazene.

The following Examples illustrate the invention. Throughout these Examples, the term "ether" refers to diethyl ether; magnesium sulphate was used to dry solutions; and reactions involving water-sensitive intermediates were performed under nitrogen. Unless otherwise stated, chromatography was performed using silica gel as the stationary phase. Where shown, infrared and NMR data are selective; no attempt is made to list every absorption. The following abbreviations are used throughout:

THF = tetrahydrofuran
s = singlet
DMF = N,N-dimethylformamide
d = doublet
GC = Gas chromatography
t = triplet
MS = Mass spectrum
m = multiplet
mp = Melting point
delta = chemical shift
ml = milliliter(s)
CDCl$_3$ = deuterochloroform
mg = milligramme(s)
J = coupling constant
g = gramme(s)
Hz = Hertz

EXAMPLE 1

This Example illustrates the preparation of the 2 geometric isomers of methyl O-methyl(2-phenoxyphenyl)oximino-acetate (compounds numbers 5 and 6 of Table I).

n-Butyl-lithium (77 ml of a 2.6 M solution in hexane) was added dropwise over 30 minutes to a stirred solution of diphenyl ether (34.0g) in dry ether (300 ml), cooled to about 0° C. The resulting orange solution was stirred at room temperature for 3 hours, allowed to stand overnight, then added dropwise over 1.5 hours to a stirred solution of dimethyl oxalate (47.0g) in dry THF (200 ml), cooled to just below 10° C. The resulting mixture was allowed to stand overnight, and was then poured into water and extracted with ether. The extracts were washed with water, dried, and concentrated under reduced pressure to give a brown oil (58.57 g). Part of this oil (12.20 g) was purified by column chromatography using 20% ether in petrol as eluant to give methyl o-phenoxybenzoylformate (5.87 g, representing 55% yield) as a pale yellow oil.

A mixture of methyl o-phenoxybenzoylformate (2.56 g) and methoxylamine hydrOchloride (1.25 g) in dry methanol (25 ml) was refluxed for about 3 hOurs and allowed to cool. Most of the solvent was removed under reduced pressure and the residue was diluted with water and extracted with ether. The extracts were washed with water, dried, concentrated under reduced pressure, and chromatographed using 20% ether in petrol to give (i) isomer A of the title compound, eluted first (0.55 g, 19% yield) as an oil; and (ii) isomer B of the title compound (1.68 g, 59% yield) as a white solid, mp 108°-111° C. An X-ray crystal structure of isomer B showed that it is the (E)-isomer.

The following are examples of compositions suitable for agricultural and horticultural purposes which can be formulated from the compounds of the invention. Such compositions form another aspect of the invention. Temperatures are given in degrees centigrade (° C), and percentages are by weight.

EXAMPLE 2

This Example illustrates the preparation of the 2 geometric isomers of methyl O-methyl (2-(E)-styrylphenyl)oximino-acetate (compounds numbers 1 and 2 of Table I).

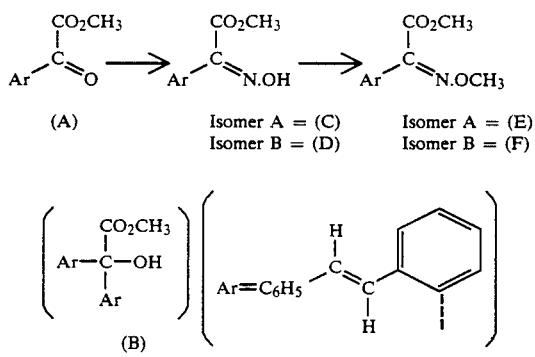

Isomer A = (C)  Isomer A = (E)
Isomer B = (D)  Isomer B = (F)

A mixture of the ketoester (A) (6.13 g, prepared by the method described in EP-A-0178826, with a purity of 54% by GC, and containing the tertiary alcohol (B) as the major impurity) and hydroxylamine hydrochloride (1.76 g) in dry methanol (100 ml) was heated under reflux for 2.5 hours. The resulting mixture was allowed to cool, and was poured into water and extracted with ether. The extracts were dried, concentrated and chromatographed using 30% ether in petrol as eluant to give (i) the oxime (C) (0.73 g, 21% yield) as an oil, eluted first and (ii) the oxime (D) (1.36 g, 39% yield), also an oil, eluted second.

A solution of the oxime (D) (1.36 g) in dry DMF (20 ml) was added dropwise to a stirred suspension of sodium hydride (0.128 g) in dry DMF (50 ml). After 10 minutes, dimethyl sulphate (0.51 ml) was added to the resulting yellow solution and the colour was discharged. After a further 30 minutes, the reaction mixture was poured into water and extracted with ether. The extracts were washed with water (x2), dried and concentrated to give a brown solid (1.44 g). This was combined with a similar batch (0.17 g) from an earlier small-scale reaction, then chromatographed to give isomer B of the title compound (F) (1.12 g, representing a yield of 70%) as a white solid, mp. 77°–78° C., with proton NMR data as shown in Table II. The oxime (C) was converted stereospecifically into isomer A of the title compound (E) (63% yield) by exactly the same method. Isomer A is an oil, with proton NMR data as shown in Table II.

EXAMPLE 3

This Example describes the preparation of a single stereoisomer of methyl O-methyl(2-methylphenyl)oximinoacetate (compound number 45 of Table I).

Dry methanol (2.5 ml) was added dropwise to a stirred suspension of sodium hydride (0.28 g) in dry ether (20 ml) to leave an almost colourless solution. To this was added a mixture of methyl (2-methylphenyl)acetate (2.0 g) and n-butyl nitrite (1.38 g) in dry ether (4 ml) to give, after an hour, a yellow suspension. After a further hour, the reaction mixture was poured into water and washed twice with ether. The resulting aqueous layer was diluted with aqueous ammonium chloride (to give a white suspension) and then extracted with ether (x3). These ether extracts were washed with water, dried and concentrated to give a viscous oil (0.52 g) containing a single stereoisomer of methyl (2-methylphenyl)oximino-acetate (70% by GC). Potassium carbonate (0.74 g) and, after 15 minutes, dimethyl sulphate (0.25 ml) were added to a stirred solution of this viscous oil in DMF (10 ml). After 2 hours, the reaction mixture was poured into water and extracted with ether. The combined extracts were washed with water, dried, concentrated and chromatographed using 20% ether in petrol as eluant to give the title compound (0.26 g, 10% yield from methyl (2-methylphenyl)acetate) as a white crystalline solid, mp. 64°–65° C., infrared (nujol mull) 1728 cm$^{-1}$, NMR (CDCl$_3$): delta 2.20 (3H,s); 3.88 (3H,s); 4.06 (3H,s) ppm.

Both stereoisomers of methyl O-methyl(phenyl)oximinoacetate were prepared from methyl benzoylformate and methoxylamine hydrochloride by the method described in Example 1. The single stereoisomer of the title compound whose preparation is described above had a very similar Rf-value on thin-layer chromatography to the more polar stereoisomer of methyl O-methyl(phenyl)oximino-acetate, and was markedly more polar than the less polar stereoisomer of methyl O-methyl(phenyl)oximino-acetate (silica gel; ether:petrol, 1:1).

EXAMPLE 4

This Example describes the preparation of a single stereoisomer of methyl O-methyl(2-(3-chlorophenoxymethyl)phenyl)oximino-acetate (compound number 39 of Table I).

A mixture of methyl O-methyl(2-methylphenyl)oximinoacetate (0.18 g, a single stereoisomer prepared as described in Example 3), N-bromosuccinimide (0.154 g) and benzoyl Peroxide (catalytic) in dry carbon tetrachloride (5 ml) was heated under reflux for 2 hours, allowed to cool, and filtered. The filtrate was concentrated under reduced pressure to give a pale yellow oil (0.25 g) containing a single stereoisomer of methyl O-methyl(2-bromomethylphenyl)oximino-acetate (NMR (CDCl$_3$): delta 3.89 (3H,s); 4.07 (3H,s); 4.34 (2H,s) ppm). Solutions of 3-chlorophenol (0.105 g) in dry DMF (1 ml) and, after 2 hours, this pale yellow oil in dry DMF (5 ml) were added to a stirred suspension of sodium hydride (0.018g) in dry DMF (10 ml). After 3 hours, the reaction mixture was poured into water and extracted with ether. The combined extracts were washed successively with water, dilute aqueous sodium hydroxide and aqueous sodium chloride, then dried, concentrated and chromatographed using 20% ether in petrol as eluant to give the title compound (0.17 g, 59% yield from methyl O-methyl(2-methylphenyl)oximinoacetate) as a white solid, mp. 53°–54° C., infrared (nujol) 1729 cm$^{-1}$, NMR (CDCl$_3$) delta 3.85 (3H,s); 4.03 (3H,s); 4.92 (2H,s) ppm.

EXAMPLE 5

An emulsifiable concentrate is made up by mixing and stirring the ingredients until all are dissolved.
Compound No. 6 of Table I: 10%
Benzyl alcohol: 30%
Calcium dodecylbenzenesulphonate: 5%
Nonylphenolethoxylate (13 moles ethylene oxide): 10%
Alkyl benzenes: 45%

EXAMPLE 6

The active ingredient is dissolved in methylene dichloride and the resultant liquid sprayed onto the granules of attapulgite clay. The solvent is then allowed to evaporate to produce a granular composition.
Compound No. 6 of Table I: 5%
Attapulgite granules: 95%

EXAMPLE 7

A composition suitable for use as a seed dressing is prepared by grinding and mixing the three ingredients.
Compound No. 6 of Table I: 50%
Mineral oil: 2%
China clay: 48%

EXAMPLE 8

A dustable powder is prepared by grinding and mixing the active ingredient with talc.
Compound No. 6 of Table I: 5%
Talc: 95%

EXAMPLE 9

A suspension concentrate is prepared by ball milling the ingredients to form an aqueous suspension of the ground mixture with water.
Compound No. 6 of Table I: 40%
Sodium lignosulphonate: 10%
Bentonite clay: 1%
Water: 49%

This formulation can be used as a spray by diluting with water or applied directly to seed.

EXAMPLE 10

A wettable powder formulation is made by mixing together and grinding the ingredients until all are thoroughly mixed.
Compound No. 6 of Table I: 25%
Sodium lauryl sulphate: 2%
Sodium lignosulphonate: 5%
Silica: 25%
China clay: 43%

EXAMPLE 114

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed on to the foliage and applied to the roots of the plants in the soil. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4 = no disease
3 = trace - 5% of disease on untreated plants
2 = 6–25% of disease on untreated plants
1 = 26–59% of disease on untreated plants
0 = 60–100% of disease on untreated plants The results are shown in Table III.

TABLE III

| COMPOUND NO. | PUCCINIA RECONDITA (WHEAT) | ERYSIPHE GRAMINIS HORDEI (BARLEY) | VENTURIA INAEQUALIS (APPLE) | PYRICULARIA ORYZAE (RICE) | CERCOSPORA ARACHIDICOLA (PEANUT) | PLASMOPARA VITICOLA (VINE) |
| --- | --- | --- | --- | --- | --- | --- |
| 1 | 0 | 0 | 3 | 0 | 0 | 4 |
| 2 | 2 | 0 | 4 | 0 | 0 | 4 |
| 3 | 0 | 0 | 4 | 0 | 0 | 0 |
| 4 | 4 | 0 | 4 | 3 | 3 | 4 |
| 5 | 0 | 3 | 3 | 1 | 0 | 0 |
| 6 | 4 | 4 | 4 | 3 | 3 | 4 |
| 7 | 0 | 1 | 3 | 0 | 0 | 3 |
| 10* | 3 | 3 | 2 | 3 | 0 | 2 |
| 13 | 0 | 0 | — | 0 | 2 | 0 |
| 17 | 3 | 0 | 1 | 0 | 0 | 2 |
| 18 | 3 | 0 | 4 | 1 | 1 | 4 |
| 32 | 4 | 3 | 2 | 0 | 1 | 4 |
| 33 | 0 | 0 | 4 | 0 | 0 | 0 |

*25 ppm foliar spray only

EXAMPLE 12

This Example illustrates the plant growth regulating properties of compounds 1, 2, 5 and 12–15 of Table I when tested on a whole plant screen against two species of plant. The plant species are identified in Table IV with the leaf stage at which they were sprayed.

A formulation of each chemical was applied at 4000 ppm (4 kg/ha in a 1000 l/ha field volume) using a track-sprayer and a SS8004E (Teejet) nozzle.

After spraying, the plants were grown in a glasshouse with 25° C. day/22° C. night temperatures. Supplementary lighting was supplied when necessary to provide an average photoperiod of 16 hours (14 hours minimum).

After 2–6 weeks in the glasshouse, depending on species and time of year, the plants were visually assessed for morphological characteristics against a control plant sprayed with a blank formulation. The results are presented in Tables V and VI.

TABLE IV

PLANT MATERIAL USED FOR WHOLE PLANT SCREEN

| Species | Code | Variety | Growth Stage at Treatment | No. Plants per 3" pot | Compost Type |
|---|---|---|---|---|---|
| Maize | MZ | Earliking | 2¼–2½ leaves | 1 | PEAT |
| Apple | AP | Red Delicious | 4–5 leaves | 1 | JIP* |

*John Innes Potting compost

TABLE V

| | | MZ | | | | |
|---|---|---|---|---|---|---|
| Compound No. | Table | R | G | A | I | P |
| 1 | I | 3 | 2 | 3 | 3 | 1 |
| 2 | I | 2 | | 2 | 2 | |
| 5 | I | 3 | | 3 | 3 | 1 |
| 12 | I | 2 | | | 1 | |
| 13 | I | 2 | | | 1 | |

TABLE VI

| | | AP | | |
|---|---|---|---|---|
| Compound No. | Table | R | G | I |
| 2 | I | 2 | 1 | 1 |
| 12 | I | 2 | 1 | 1 |
| 13 | I | 2 | 1 | 1 |
| 14 | I | 1 | 1 | 1 |
| 15 | I | 1 | 1 | 1 |

KEY
R = Retardation
G = Greening effect
A = Apical damage
I = Interligular or internodal length reduction
P = Phytotoxicity
All effects except phytotoxicity, are scored visually on a 1–3 basis where
1 = 10–30%
2 = 31–60%
3 = 61–100%
Blank means less than 10% effect.
Phytotoxicity is scored on a 1–5 basis where
1 = less than 10%
2 = 11–30%
3 = 31–50%
4 = 51–70%
5 = greater than 70%
Blank means no effect at all observed.

We claim:

1. A compound having the general formula (I):

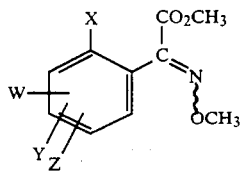

and stereoisomers thereof, wherein X is cycloalkyl, aralkyl in which the alkyl moiety is optionally substituted with hydroxy or $C_{1-4}$ alkoxy, aryloxyalkyl in which the alkyl moiety is optionally substituted with methoxy, alkenyl, optionally substituted with phenyl, furyl, thienyl or pyridyl, alkynyl optionally substituted with phenyl, aryl, amino optionally substituted with aryl or alkyl, arylazo in which the aryl moiety is optionally substituted with alkylnyl, alkoxy or dialkyl-amino, heteroarylalkyl, heteroaryloxyalkyl, acylamino in which the amino group is optionally substituted with alkyl, nitrilo, trifluoromethyl, -OR', SR', -$CO_2R^2$, -$CONR^3R^4$, -$COR^5$, -$CR^6=NR^7$, -$N=CR^8R^9$, -$SOR^{10}$ or -$SO_2R^{11}$; W, Y and Z, which may be the same or different, are any of the atoms or groups listed for X above and, in addition, may be hydrogen or halogen atoms or alkyl, alkoxy, alkylthio or nitro; or any two of the groups W, X, Y and Z, in adjacent positions on the phenyl ring, optionally join to form a fused ring, either aromatic or aliphatic, optionally containing one or more heteroatoms; R' is cycloalkyl optionally containing a heteroatom in the cycloalkyl ring, alkenyl optionally substituted as alkenyl above, acyl, aryl, heteroaryl, aralkyl optionally substituted as aralkyl above or heteroarylalkyl; $R^2$, $R^3$, $R^4$, $R^5$, $R^6$, $R^8$, $R^9$, $R^{10}$ and $R^{11}$, which may be the same or different, are hydrogen or alkyl, cycloalkyl, cycloalkylalkyl, alkenyl optionally substituted as alkenyl above, aralkyl optionally substituted as aralkyl above, aryl or heteroaryl; and $R^7$ is aryl; except where otherwise stated, any foregoing alkyl group or moiety being optionally substituted with hydroxy, halogen or alkoxycarbonyl and any foregoing aryl or heteroaryl group or moiety being optionally substituted with one or more of halogen, hydroxy, $C_{1-4}$ alkyl, $C_{1-4}$ alkoxy, trifluoromethyl, trifluoromethoxy, phenoxy, benzyloxy, nitro, amino, phenyl, carboxy or carboxylic acid ester, cyano, alkylcarbonylamino or methylenedioxy, the phenoxy and benzyloxy groups being optionally substituted with any of those other substituents which may be present on aryl groups or moieties provided that when W, Y and Z are independently hydrogen, or alkyl X is not phenylalkyl, phenoxyalkyl, phenylalkenyl, phenylalkynyl, OR' in which R' is phenyl or phenylalkyl, or any such group in which the phenyl moiety is substituted with halogen, $C_{1-4}$ alkyl, $C_{1-4}$ alkoxy, trifluoromethyl, unsubstituted or halo or alkyl substituted phenoxy, unsubstituted or halo or alkyl substituted benzyloxy, nitro, phenyl or cyano.

2. A compound according to claim 1 in which X is optionally substituted aralkyl, optionally substituted heteroarylalkyl, optionally substituted aryloxyalkyl, optionally substituted heteroaryloxyalkyl, optionally substituted alkenyl, optionally substituted alkynyl, optionally substituted acylamino, -$OR^1$, -$SR^1$ or -$CO_2R^2$; W, Y and Z, which are the same or different, are single atoms or sterically small groups; or W and X, when in adjacent positions on the phenyl ring, join to form a fused ring, either aromatic or aliphatic, optionally containing one or more heteroatoms; $R^1$ is optionally substituted aryl, optionally substituted heteroaryl, optionally substituted aralkyl or optionally substituted heteroarylalkyl and $R^2$ is optionally substituted alkyl or optionally substituted aryl.

3. A compound according to claim 2 in which optionally substituted alkenyl is optionally substituted aryl- or optionally substituted heteroaryl-ethenyl, optionally substituted alkynyl is optionally substituted aryl- or optionally substituted heteroaryl-ethynyl, and optionally substituted acylamino is optionally substituted aryl- or optionally substituted heteroarylcarbonylamino 4. A compound according to claim 1 in which X is a group Ar-A- wherein A is a linking group selected from O, S, CHR'CHR", CH=CH, C=C, OCHR', CHR'O, $O_2C$ and CONR', R' and R" are independently hydrogen or methyl and Ar is aryl, heteroaryl or cyclohexyl, the aryl and heteroaryl moieties being optionally substituted with halo, methyl, methoxy or nitro; and W, Y and Z are independently hydrogen, fluoro, chloro, methyl or methoxy, or when W is in an adjacent position to X on the phenyl ring, Ar is phenyl and A is O or S, W joins Ar at the carbon atom adjacent to that attached to A, optionally via a linking oxygen or sulphur atom, to form a fused ring.

5. A compound according to claim 4 in which A is O or CH=CH and Ar is furyl or phenyl optionally substituted with fluoro, chloro, methoxy or nitro and W, Y and Z are hydrogen.

6. A fungicidal composition comprising, as an active ingredient, a compound of formula (I) as defined in claim 1 and a fungicidally acceptable carrier or diluent therefor.

7. A method of combating fungi, which comprises applying to a plant, to a seed of a plant, or to the locus of the plant or seed, a fungicidally effective amount of a compound as defined in claim 1.

8. A method of regulating plant growth which comprises applying to a plant, to a seed of a plant or to the locus of the plant or seed, an effective amount of a compound as defined in claim 1.

* * * * *